United States Patent [19]

Bloom et al.

[11] Patent Number: 4,483,338
[45] Date of Patent: Nov. 20, 1984

[54] BI-POLAR ELECTROCAUTERY NEEDLE

[75] Inventors: William G. Bloom, Menlo Park; Gary I. Geschwind, Palo Alto, both of Calif.

[73] Assignee: Raychem Corporation, Menol Park, Calif.

[21] Appl. No.: 272,853

[22] Filed: Jun. 12, 1981

[51] Int. Cl.³ .............................................. A61B 17/39
[52] U.S. Cl. ............................ 128/303.13; 128/303.18
[58] Field of Search .............. 128/642, 303.13, 303.14, 128/303.15, 303.17, 303.18, 784; 339/DIG. 1; 174/DIG. 8

[56] References Cited

U.S. PATENT DOCUMENTS

| | | | |
|---|---|---|---|
| 2,763,935 | 9/1956 | Whaley et al. | 128/303.18 X |
| 3,339,411 | 9/1967 | Riffie | 339/DIG. 1 |
| 3,513,429 | 5/1970 | Helsup | 339/DIG. 1 |
| 3,651,812 | 3/1972 | Samuels | 128/303.18 |
| 3,682,162 | 8/1972 | Colyer | 128/303.18 X |
| 3,721,749 | 3/1973 | Clabburn | 174/88 R |
| 3,911,241 | 10/1975 | Jarrard | 128/303.17 X |
| 4,034,762 | 7/1977 | Cosens et al. | 128/303.18 X |
| 4,076,028 | 2/1978 | Simmons | 128/303.17 X |
| 4,178,067 | 12/1979 | Johnson et al. | 350/96.21 |
| 4,227,293 | 10/1980 | Taylor | 29/447 |

FOREIGN PATENT DOCUMENTS

| | | | |
|---|---|---|---|
| 2235666 | 1/1975 | France | 128/642 |
| 2252191 | 6/1975 | France . | |

Primary Examiner—Lee S. Cohen
Attorney, Agent, or Firm—Ira D. Blecker; James W. Peterson; Herbert G. Burkard

[57] ABSTRACT

A bi-polar electrocautery needle comprising an inner electrode, an outer electrode and recoverable insulating-locking member for insulating the electrodes from one another and locking them into relative position to one another. And the method of making the bi-polar electrocautery needle in accordance with this invention, the steps including: expanding recoverable dielectric material over an inner electrode; inserting the combination into an outer electrode, and recovering the material between the electrodes for insulating and locking the electrodes into relative position with one another.

9 Claims, 11 Drawing Figures

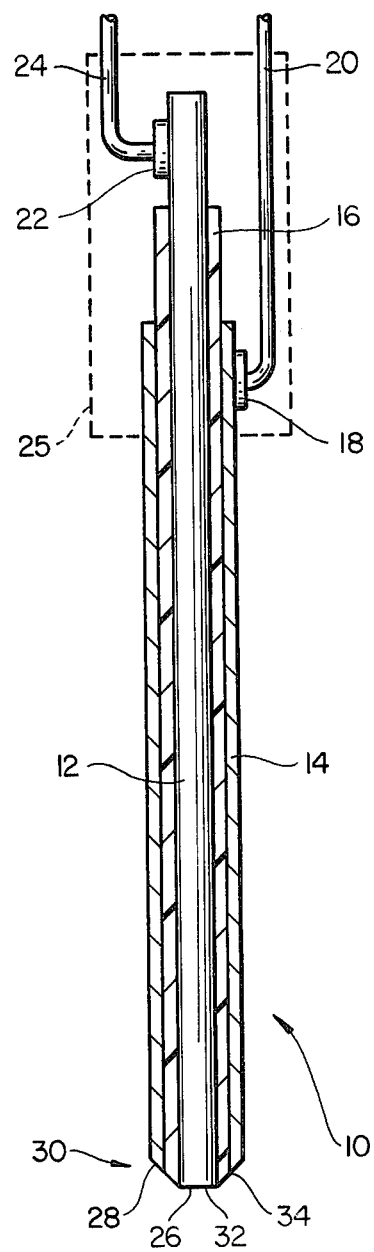
FIG_1
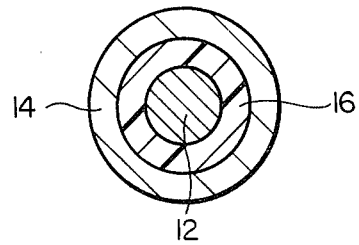
FIG_2

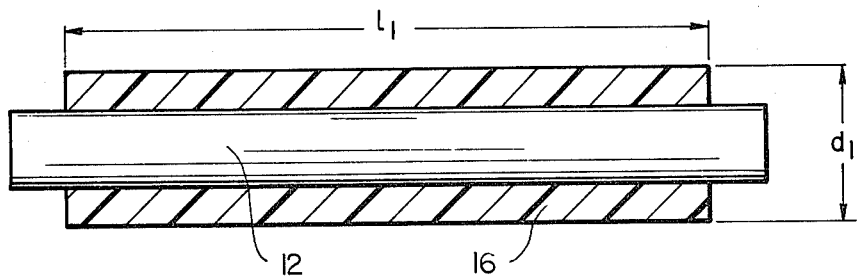
FIG_3A
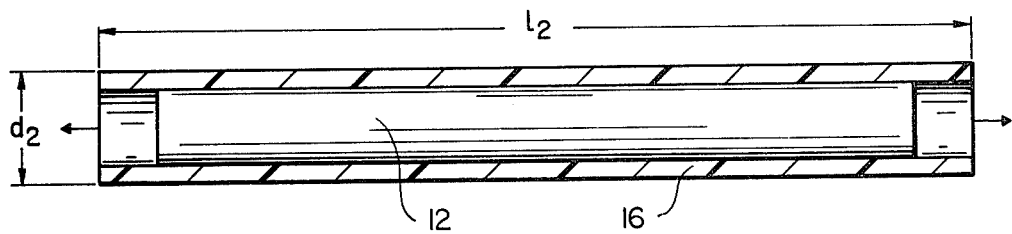
FIG_3B
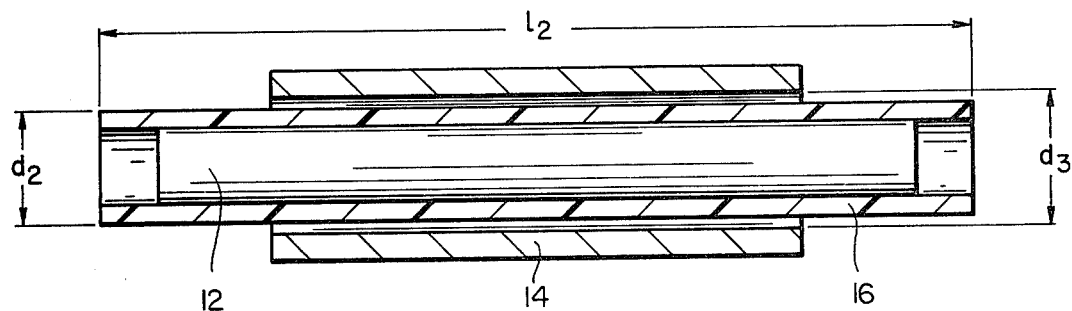
FIG_3C
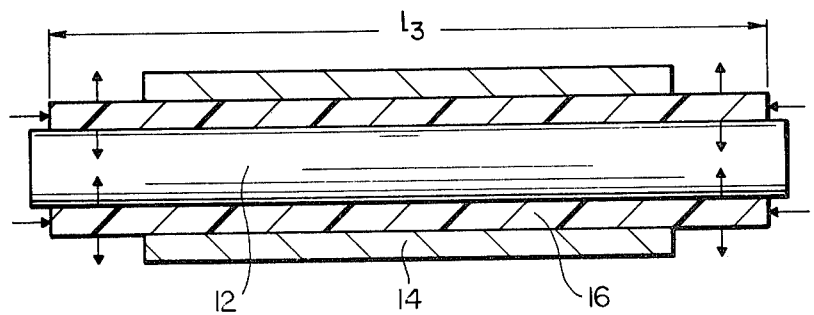
FIG_3D

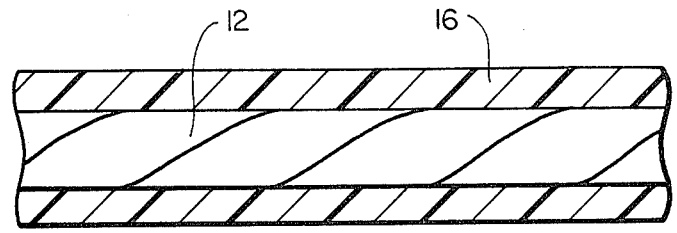
FIG_4A
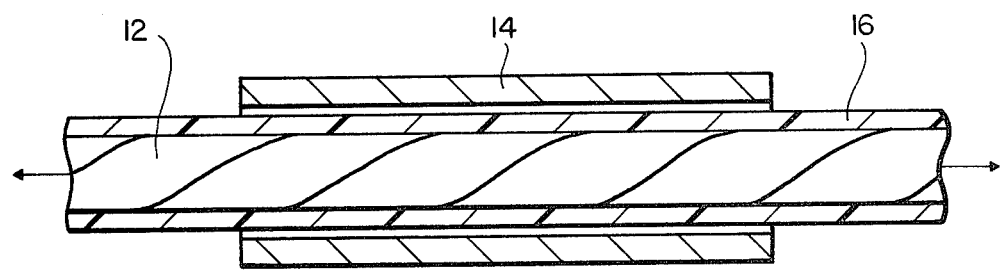
FIG_4B
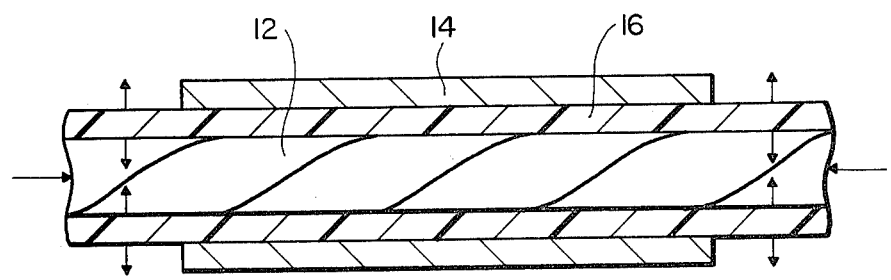
FIG_4C

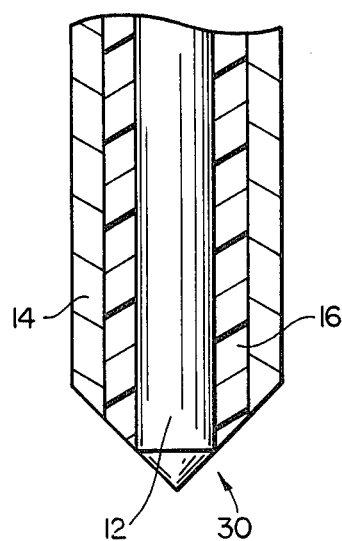
FIG_5A
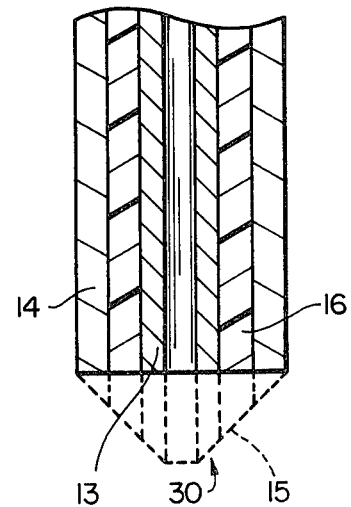
FIG_5B

BI-POLAR ELECTROCAUTERY NEEDLE

BACKGROUND OF THE INVENTION

Bi-polar electrocautery tools have been used for a variety of electrosurgical procedures. For example, where a very controlled, localized current concentration is required, such as neuro- and eye surgery the bi-polar needle is especially useful. Currently, for these procedures, a forcep type probe is used. Each leg of the forcep is electrically isolated and insulated up to the extreme end of the tip. Only when the ends of the tip are brought into close proximity is there current flow, and then only across the gap between the tips. While this structure permits extremely accurate surgical procedures involving only minute amounts of tissue, the area of tissue burn must first be exposed to be reached with the forceps. Typically, a substantial amount of surgical cutting is required to locate the correct site for such forcep type electro-needles. Further, typical needles are expensive and not disposable, which leads to a variety of maintenance problems, including cleaning, resterilization, and maintenance of extremely delicate surgical instruments.

Applicants have developed an inexpensive bi-polar needle designed to be disposable. Bi-polar tools are not new; they have been known for some time. Typical bi-polar tools include an inner and outer electrode and an intermediate layer of epoxy. The epoxy layer tends to break down upon the above described maintenance. These bi-polar tools are exemplified by Colyer, U.S. Pat. No. 3,682,162, which includes a small diameter hypodermic needle inserted into a larger diameter hypodermic needle and bonded together with an epoxy resin or other thermosetting plastic material as an intermediate layer. The history of such bi-polar needles are summarized in Cosens et al., U.S. Pat. No. 4,034,762, which is incorporated herein by reference. Cosens et al. recognized the problem of such bi-polar needles, and created a needle which could be re-usable and withstand the rigors of maintenance. For instance, as seen in FIGS. 1 and 2 of Cosen et al., a cap 12 is required to hold the electrodes together while dielectric tubing is used to insulate the electrodes. However, even Cosens et al. uses epoxy to secure the outer electrode to the cap 12.

Applicant's structure relies upon the natural properties of elastomeric heat-recoverable materials to fix the position of the electrodes with respect to each other. Further, applicants select the elastomeric heat-recoverable material of a proper dielectric constant for correct insulation. In applicants' preferred embodiment, they use a cross-linked polymeric heat-recoverable material which can withstand the high power output which may be carried by applicants' electrodes without experiencing break down.

While cross-linked material is not new to the field of catheter manufacture, such material has not been found to be used for joining bi-polar electrodes nor for insulating the same as claimed by applicants here. For instance, Taylor,f U.S. Pat. No. 4,227,293, discloses a catheter having a flexible annular balloon secured to a shaft of the catheter by a pair of annular sleeves. The annular sleeves are typically of a cross-linked material and are shrunk over the grooves of the shaft to hold the flexible annular balloon to the catheter shaft. This type of structure is clearly different from applicants' claimed structure.

SUMMARY OF THE INVENTION

Applicants have discovered a bi-polar electrocautery needle comprising an inner electrode, an outer electrode, and including an intermediate zone which defines an insulating-locking means. The means is first axially stretched and thereby radially reduced to accomodate the slipping on of the outer electrode over the inner electrode so that the outer and inner electrodes may be concentric. The means is then recovered to its normal, radially larger condition. The means being in compression thereby exerts a force in the radial direction on both electrodes, locking the electrodes into fixed relation to one another. Since the means is made from a dielectric material, it also serves the purpose of insulating the electrodes from each other.

The method for making a bi-polar electrocautery needle in accordance with this invention is also described herein and includes the steps of stretching an insulating-locking means made from dielectric material over an inner electrode; slipping an outer electrode over the means and inner electrode; and recovering the means to its radially larger condition, locking the electrodes in fixed relation to one another, while insulating the electrodes from one another.

OBJECTS OF THE INVENTION

It is an object of this invention to provide a bi-polar electrocautery needle which is inexpensive to manufacture.

It is another object of this invention to provide an electrocautery needle which can withstand high power without failure.

It is another object of this invention to provide an inexpensive method for making the bi-polar needle in accordance with this invention.

It is another object of this invention to provide a bi-polar electrocautery needle which is capable of being easily connected to a power source.

It is another object of this invention to provide a bi-polar electrocautery needle which includes an end that may be ground into a tip.

It is another object of this invention to provide a bi-polar electrocautery needle which includes an end that may be formed easily into a tip of various configurations.

DESCRIPTION OF THE DRAWING

FIG. 1 is a cross-sectional view of a bi-polar electrocautery needle in accordance with this invention.

FIG. 2 is a cross-sectional view of a bi-polar electrocautery needle in accordance with this invention taken along cross-section line 2—2 of FIG. 1.

FIGS. 3 A, B, C, and D are schematic illustrations of the steps for making the bi-polar electrocautery needle in accordance with this invention.

FIGS. 4 A, B, and C are schematic illustrations of the steps for an alternative method of making the bi-polar electrocautery needle in accordance with this invention.

FIGS. 5A and 5B are cross-sectional views of alternate electrode tip configurations.

DETAILED DESCRIPTION OF THE INVENTION

Referring to the drawings, wherein like reference characters designate like or corresponding parts throughout the several views, and referring particularly to FIGS. 1 and 2, there is shown a bi-polar electrocautery needle generally designated by the numeral 10.

The bi-polar electrocautery needle includes an inner electrode 12 which may be either hollow or solid depending upon user needs. The bi-polar electrocautery needle includes an outer electrode 14 which as seen in FIG. 2 is concentric with the inner electrode 12. Intermediate the electrodes 12 and 14 is an insulating-locking means 16.

The insulating-locking means 16 may be elastic, meaning that when stretched from its normal condition having length $l_1$ and diameter $d_1$, it tends to recover thereto. The means may further be heat-recoverable, meaning when stretched the means may be recoverable to its original condition by heating. As will be appreciated, when stretching such a means axially, it also deforms radially, reducing its outside diameter. Applicants choose the outside diameter of the means 16 to be larger than the inside diameter $d_3$ of the outer electrode 14. With the means 16 in the unstretched condition, the outer electrode 14 could not be slipped over the inner electrode 12 with means 16.

As shown in FIG. 3B, applicants axially stretch means 16 in the direction of the arrows to length $l_2$, thereby radially reducing the means to diameter $d_2$ which is less than $d_3$. As illustrated in FIG. 3C the outer electrode 14 is then slipped over the inner electrode 12 and stretched means 16. After correctly positioning the electrodes relative to one another, the means is recovered or relaxed as illustrated in FIG. 3C. Since the means is elastic or heat-recoverable, it attempts to return to its normal diameter $d_1$ and length $l_1$. Of course, since the outside diameter $d_1$ of the means 16 is greater than the inside diameter $d_3$ of the outer electrode 14, the normal dimensional condition ($l_1$ and $d_1$) of the means 16 will not be fully realized. Instead, the means since it is in compression will continuously and continually assert a radial force against the electrodes 12 and 14 in the direction of the arrows of FIG. 3D, thereby locking the electrodes in relative position to one another.

The means 16 is made from material having the desired dielectric constant. Among the materials which fulfill both the locking and the dielectric properties are Tefzel*. Thus, the means 16 serves as a locking and insulating means as described above.

*Registered Trademark of E. I. duPont deNemours & Co.

The means 16 is preferably a heat recoverable, polymeric cross-linked material so that it may withstand high power carried by the electrodes. As is well-known, cross-linked materials do not melt at temperatures above their transition states. (See, e.g. U.S. Pat. No. 3,721,749.) When applicant uses high power through the electrodes, the temperature is quite hot, and would ordinarily melt such materials. Cross-linked polymeric materials do not suffer these such problems and therefore are quite useful when high power (greater than 50 watts) is used.

In previous bi-polar needles, particularly Colyer, U.S. Pat. No. 3,682,162, the intermediate layer would break down and fail to perform its insulating function when high voltage (greater than 10 watts) is carried by the electrodes. Colyer specifically limited this structure to a bi-polar needle carrying between 1 to 10 volts at 100 miliamps or maxium of 1 watt. Applicant here provides a structure capable of withstanding 100 or more watts.

Applicants, in the preferred embodiment, choose the recovered length of the means $l_3$ to be less than the length of the inner electrode. Applicants further choose the length of the outer electrode to be less than $l_3$. This enables the assembled bi-polar needle to be easily connected to a power source since, as illustrated in FIG. 1, electrodes 12 and 14 may be easily connected to power source at one end, while the other end may be ground into a tip.

The electrodes 12 and 14 may be joined to leads as shown in FIG. 1. Joining means 18 connects electrode 14 to an electrical lead 20, and a joining means 22 connects electrode 12 to another electrical lead 24. The needle may then be inserted into a handle or directly tied to a power source. In use, the handle portion 25 insulates the electrical current carried by the electrode so as not to cause shock or other uncomfortable side effects.

In the ordinary course, the user will install the needle 10 into a handle 25, which would be tied to a power source. Since the bi-polar needle 10 is inexpensive, it may then be used and disposed of without the need for cleaning.

The electrodes are terminated as shown at ends 26 and 28 into a tip 30. Using applicants' system, it is possible to easily form the type of tip desired. In configuration shown, the tip 30 may be formed having a flat section 32 with cantilevered side 34. It will be appreciated that where the inner electrode 12 is a solid electrode, it may be desirable to sharpen the tip 30 to a pencil point-like structure for generating short current path across the ends 26 and 28 of the electrodes 12 and 14, respectively.

FIG. 5A illustrates tip 30 sharpened to a pencil-point-like structure wherein the inner electrode 12 is a solid electrode.

FIG. 5B illustrates a hollow inner electrode 13 which may also be sharpened as shown in phantom at 15.

Alternatively, applicants have found that it may be possible to form the bi-polar needle in a less expensive manner as shown in FIGS. 4 A, B, and C. In this case, applicants use a pre-made insulated wire. The wire includes an inner core such as 12 and a dielectric jacket, heat-recoverable material comprising the means 16. The wire is expanded, preferably the outer material only, to an axially stretched, radially reduced condition. As seen in FIG. 4B, an outer electrode such as 14 may then be slipped over the stretched wire and recovered in the fashion described above and illustrated in FIG. 4C. Thus, for manufacturing ease, applicants have found that it is desirable to select a particular diameter wire already having the insulating-locking means. Preferably the jacket comprising is pre-expanded before being extruded over the core. Particularly, applicants have found Raychem's 55 Wire[1] having a Tefzel[2] jacket of pre-expanded Tefzel[2] to be especially useful for the above described embodiment.

[1]Registered Trademark of Raychem Corporation [2]Registered Trademark of E. I. duPont deNemours & Co.

While the instant invention has been described by reference to what is believed to be the most practical embodiments, it is understood that the invention may embody other specific forms not departing from the spirit of the central characteristics of the invention. It should be understood that there are other embodiments which possess the qualities and characteristics which would generally function in the same manner and should be considered within the scope of this invention. The present embodiments therefore should be considered in all respects as illustrative and not restrictive, the scope of the invention being limited solely to the appended claims rather than the foregoing description and all equivalents thereto being intended to be embraced therein.

What is claimed is:

1. A bi-polar electrocautery needle, comprising:
   an inner electrode;
   an outer electrode concentric with the inner electrode; said electrodes having one end defining an operable tip and an opposed end adapted to be connected to a source of power; and
   insulating-locking means disposed between the electrodes, the insulating-locking means being in compression exerting a force in the radial direction on both electrodes, said insulating-locking means locking the electrodes in fixed relation to one another and insulating the electrodes from each other.

2. The needle as set forth in claim 1 wherein the insulating-locking means comprises a polymeric heat recoverable material.

3. The needle as set forth in claim 1 wherein the insulating-locking means comprises a cross-linked polymeric material which is heat recoverable and capable of withstanding high electrical power carried by the electrodes.

4. The needle as set forth in either claim 1 or claim 3 wherein the inner electrode is solid.

5. The needle as set forth in claim 4 wherein the one end of the electrodes is ground into a pencil point-like tip for generating short current paths.

6. The needle as in claim 1 or claim 3 wherein the inner electrode is hollow.

7. The needle as set forth in claim 6 wherein the one end of the electrodes is ground to a tip for generating short current paths.

8. The needle as set forth in claim 3 wherein the electrodes comprise substantially uniform cross-section tubular electrodes.

9. The needle as set forth in claim 1 wherein the means comprises cross-linked heat recoverable Tefzel[1].

[1] Registered Trademark of Raychem Corporation

* * * * *